US00PP12226P2

(12) United States Plant Patent
Littlejohn

(10) Patent No.: US PP12,226 P2
(45) Date of Patent: Nov. 27, 2001

(54) ORNITHOGALUM PLANT NAMED 'ORANJEZICHT'

(75) Inventor: Gail Littlejohn, Elsenburg (ZA)

(73) Assignee: ARC Roodeplaat, Elsenburg (ZA)

( * ) Notice: Subject to any disclaimer, the term of this patent is extended or adjusted under 35 U.S.C. 154(b) by 0 days.

(21) Appl. No.: 09/163,331

(22) Filed: Sep. 30, 1998

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM JOUVE Computerized Database, citations for 'Oranjezicht', Mar. 1999.*

* cited by examiner

*Primary Examiner*—Bruce R. Campell
*Assistant Examiner*—Wendy C Baker
(74) *Attorney, Agent, or Firm*—Foley & Lardner

(57) ABSTRACT

A new and distinct cultivar of *Ornithogalum dubium* named 'Oranjezicht', particularly characterized by its tepal color of 25A RHS; leaf color of 137A RHS; lanceolate leaves and leaves which grow relatively flat on the ground.

1 Drawing Sheet

The present invention comprises a new and distinctive cultivar of Ornithogalum, botanically known as *O. dublium* and hereinafter referred to by the cultivar name 'Oranjezicht'. The genus Ornithogalum contains approximately 100 species of bulbous perennials native to Africa, Europe, and Western Asia. Most members of the genus are winter- and spring-flowering.

Under natural conditions, 'Oranjezicht' grows during the autumn and winter and flowers in the spring. 'Oranjezicht' has a short dormant phase in summer. When the cultivar is transplanted from in vitro propagation, it remains vegetative until the bulb is large enough and then flowers. The leaves grow fairly flat on the ground.

BACKGROUND OF THE INVENTION

'Oranjezicht' is a product of a planned breeding program, which had the objective of creating new Ornithogalum cultivars to expand the characteristics of cultivars available in the market place. 'Oranjezicht' was originated from a hybridization made by the inventor in a controlled breeding program in ARC Finjnbos Unit, Private Bag X1, 7607 Elzenburg, South Africa in October 1994. The female and male parents were proprietary selections of *O. dubium.* 'Oranjezicht' was discovered and selected as one flowering plant within the progeny of the stated cross by Gail LITTLEJOHN on November 1995 in a controlled enviroment in Elzenburg, South Africa.

The first act of asexual reproduction of 'Oranjezicht' was accomplished by in vitro propagation in a controlled environment in ARC Roodeplaat (Western Cape), Mudersvlei Road, Elzenburg, South Africa.

Horticultural examination of selected units has demonstrated that the combination of characteristics as herein disclosed for 'Oranjezicht' are firmly fixed and are retained through successive generations of asexual reproduction.

'Oranjezicht' has not been observed under all possible environmental conditions. The phenotype may vary significantly with variations in environment, such as temperature, light intensity, and day length, without, however, variance in genotype. The following observations, measurements, and comparisons describe plants grown in Elzenburg, South Africa under conditions which approximate those generally used in commercial practice.

The following traits have been repeatedly observed and are determined to be basic characteristics of 'Oranjezicht' which, in combination, distinguish this Ornithogalum as a new and distinct cultivar.

BRIEF SUMMARY OF THE INVENTION

'Oranjezicht' is particularly characterized by the following characteristics:

1. Tepal Color of 25A RHS;
2. Leaf Color of 137A RHS;
3. Lanceolate leaves; and
4. Leaves which grow relatively flat on the ground.

BRIEF DESCRIPTION OF THE DRAWING

The accompanying photographic drawing shows typical plant and flower characteristics of 'Oranjezicht', with colors being as true as possible with illustrations of this type. In the following description, color references are made to The Royal Horticultural Society Colour Chart (R.H.S.). The color values were determined between 11 a.m. and 12 p.m. at ARC Fijnbos, Elzenburg, South Africa.

DETAILED BOTANICAL DESCRIPTION

The following traits have been repeatedly observed and, in combination, distinguish 'Oranjezicht' as a new and distinct cultivar. These observations, measurements and descriptions were taken for 'Oranjezicht' grown under greenhouse conditions which were approximately those generally used in commercial practice:

Origin: Breeding program.
Parentage:
*Female parent.*—Proprietary selection of *O. dubium.*
*Male parent.*—Proprietary selection of *O. dubium.*
Classification:
*Botanical.*—*Ornithogalum dubium.*

Plant:

*Height.*—The total height of the flowering plant is approximately 260 mm.

*Size.*—Approximately 140 mm in diameter at a flowering age of about two years when grown in a glass fiber tunnel.

*Stems.*—Length (without inflorescence): approx. 120 mm. Diameter: 6 mm.

*Foliage.*—Quantity: approx. 7. Size of leaf: Length: approx. 100 mm. Width: 5–40 mm. Shape of Leaf: Lanceolate. Color: Upper surface dark green, RHS 137A to 137B in winter, RHS 147A in spring, lower surface green RHS 137B. Habit: Leaves grow relatively flat on the ground.

*Height.*—Approximately 30 mm.

*Margin.*—Smooth.

*Bulb.*—Size: Diameter 21 mm. Color: White, RHS 155D, (1–2 layers of light brown scales form around bulb when dry). Shape: Round to oblate.

Inflorescence:

*Organization.*—Corymbose raceme with approx. 20 flowers.

*Width of flower umbel.*—80 mm.

*Number of flower buds.*—14 in winter; 14–20 in spring.

*Number of calyxes.*—6.

*Quality of bloom.*—165 days in winter; 120 days in spring.

Flower:

*Size.*—Approximately 50–60 mm in diameter.

*Shape.*—Funnelform.

*Number.*—A simple raceme has approximately 18 flowers.

*Stamens.*—Number: 6.*Color:* 174B RHS.

*Pistils.*—Color: 147B RHS.

*Styles.*—Number: 1. Color: Black.

*Tepals.*—Number: Approximately 6. Length: Approx. 25–27 mm. Width: Approx. 15–19 mm

*Number.*—6.

*Color.*—Inner and outer tepal surfaces are RHS 25A to 25D RHS in winer; 28A RHS in spring.

*Inner center coloration of the flower.*—Brown, RHS 200B, at tepal base, as is typical of the species.

*Duration of bloom.*—Approximately 5 weeks.

*Lastingness of individual bloom.*—Approximately 1 week.

*Fragrance.*—Citrus type.

*Seed/fruit.*—Seed capsules are only formed when deliberately pollinated by hand since flowers are sterile when pollinated by their own pollen. Seeds are approximately 1 mm in length, black and comma-shaped. The oblong capsule is approximately 15 mm in length.

*Cold/heat tolerance.*—At temperatures below freezing, the leaves become damaged. At high temperatures, the leaves die since the plant remains dormant in the natural habitat during hot, summer months.

*Resistance/susceptibility to disease.*—Very susceptible to Ornithogalum mosaic virus; some problems with Erwinia and Helminthosporium spp. can be expected.

I claim:

1. A new and distinct cultivar of Ornithogalum plant named 'Oranjezicht' as illustrated and described.

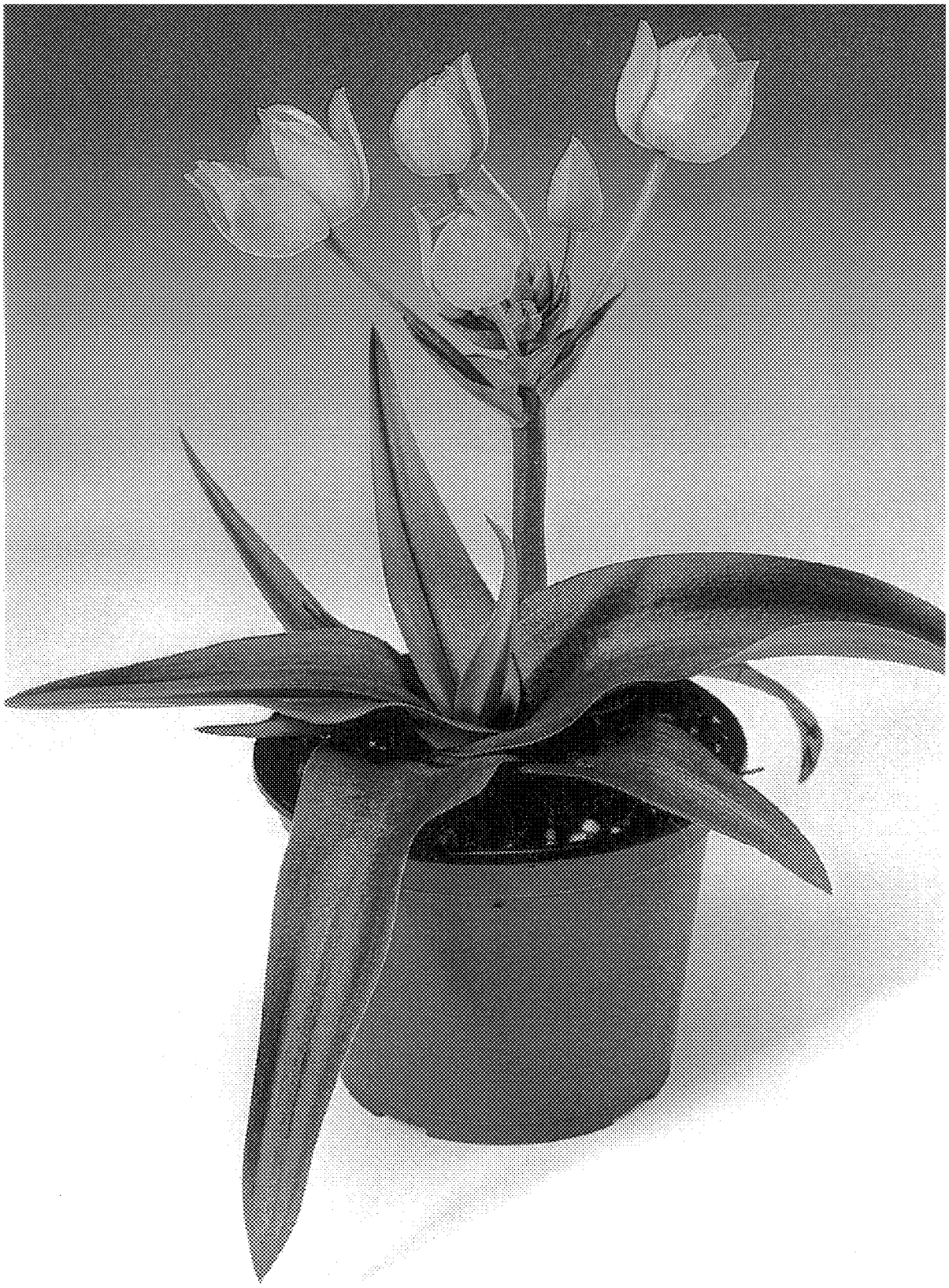

* * * * *